United States Patent [19]

Hanada et al.

[11] Patent Number: 5,070,318
[45] Date of Patent: Dec. 3, 1991

[54] EXHAUST GAS SENSOR AND PROCESS FOR PRODUCING SAME

[75] Inventors: Mariko Hanada, Nara; Kazuo Okino, Hyoogo; Kazunari Komatsu, Hiroshima, all of Japan

[73] Assignee: Figaro Engineering, Inc., Osaka, Japan

[21] Appl. No.: 323,898

[22] Filed: Mar. 15, 1989

[30] Foreign Application Priority Data

Mar. 15, 1988 [JP] Japan ................................. 63-61222

[51] Int. Cl.$^5$ ............................................... H01C 7/00
[52] U.S. Cl. ....................................................... 338/34
[58] Field of Search ...................... 338/34, 35; 73/863, 73/27 R; 422/98; 423/593

[56] References Cited

U.S. PATENT DOCUMENTS 4,701,739 10/1987 Sasaki ..................................... 338/34
4,816,800 3/1989 Onaga et al. ........................... 338/34
4,911,914 3/1990 Satake et al. ......................... 423/593

FOREIGN PATENT DOCUMENTS 61-155947 7/1986 Japan .
62-58149 3/1987 Japan .
2149121 2/1987 United Kingdom .

OTHER PUBLICATIONS

Proceedings of 2nd Int. Meetings on Chemical Sensors, Bordeaux 1986 1-08 (pp. 138-141) Shimuzu et al.
Proceedings of 2nd Int. Meetings on Chemical Sensors, Bordeaux 1986 1-09 (pp. 142-145) Arai et al.

Primary Examiner—Bruce A. Reynolds
Assistant Examiner—Marvin M. Lateef
Attorney, Agent, or Firm—Kerkam, Stowell, Kondracki & Clarke

[57] ABSTRACT

An exhaust gas sensor containing $BaSnO_3$ or the like and a process for producing the sensor. The $BaSnO_3$ is made free of segregation and adapted to have acid-base strength of at least 6.8 as determined with Hammett's indicator. Causes to reduce the acid-base strength of the $BaSnO_3$ includes presence of Si and B, and causes to increase the acid-base strength include addition of Mg or Ca. The desired $BaSnO_3$ can be prepared by precipitating $BaSnO_3$ hydrous crystals while preventing introduction of Si and B thereinto especially with use of a container lined with a synthetic resin to prevent introduction of Si and B from the container, adding Mg or Ca to the precipitate, and thermally decomposing the precipitate.

4 Claims, 11 Drawing Sheets

EXHAUST GAS SENSOR AND PROCESS FOR PRODUCING SAME

FIELD OF THE INVENTION

The present invention relates to exhaust gas sensors and a process for producing the same, and more particularly to exhaust gas sensors incorporating a perovskite metallic oxide semiconductor and a process for producing such sensors. The invention is based on the findings obtained as to the relationship between the characteristics of the perovskite compound used and the acidity-basicity thereof. The invention further relates to the elimination of the influence of Si and B impurities on perovskite compounds.

The exhaust gas sensors of the invention are useful for detecting oxygen, combustible gases, etc., especially for detecting the composition of exhaust gas from motor vehicle engines.

PRIOR ART

We have clarified the relationship between the characteristics of $BaSnO_3$ and the segregation of Ba and Sn elements therein (Japanese Patent Application SHO 61-230,288, corresponding U.S. patent application Ser. No. 101,762, European Laid-Open Patent Application 8711,4147.9 and R.O.K. Patent Application 1987-10,789). When Ba atoms and Sn atoms are not fully mixed together microscopically, segregation of Ba or Sn occurs in $BaSnO_3$. The $BaSnO_3$ containing segregates is unstable. For example, when such a compound is used as installed in the exhaust pipe extending from a motor vehicle engine, the compound reacts with P or the like in the exhaust gas to undergo decomposition. In contrast, when free of segregation, the compound exhibits enhanced durability in the exhaust gas and becomes more resistant to various poisoning atmospheres, further exhibiting improved sensitivity to oxygen and a higher speed of response to changes in atmosphere.

$BaSnO_3$, when free of segregation, is microscopically uniform in composition within crystals and therefore distinctly reflects the influence of a very small amount of impurities.

We have found that the characteristics of $BaSnO_3$ are dependent largely on Si and B as impurities. These impurities are introduced into the compound chiefly during the precipitation process of hydrous crystals of $BaSnO_3$ from the glass container used for the process.

Unexamined Japanese Patent Application SHO 62-58,149, a prior-art reference concerned, discloses that 1 to 40 mole % of an alkaline earth element is added to $BaSnO_3$, which, however, involves segregation. Since the $BaSnO_3$ with segregation has microscopically uneven crystals, the influence of traces of additives or impurites thereon differs from that on segregation-free $BaSnO_3$.

SUMMARY OF THE INVENTION

To provide an improved exhaust gas sensor incorporating $BaSnO_3$, $SrSnO_3$, $CaSnO_3$ or like compound, an object of the present invention is
(1) to inhibit variations in the sensor resistance,
(2) to improve the speed of response to changes in the ambient atmosphere at low temperatures,
(3) to improve the durability of sensor against various atmospheres, and
(4) to inhibit Sn element from $BaSnO_3$ or the like from forming a solid solution in the electrodes used in the sensor.

Another object of the invention is to provide a process for producing an exhaust gas sensor without permitting the introduction of Si and B into the sensor since these elements would impair the sensor characteristics.

Another object of the invention is to provide a process for preparing perovskite compounds by a liquid-phase reaction with a reduced likelihood of contamination with impurities from the container so that the process can be employed generally in producing exhaust gas sensors with use of various perovskite compounds.

Up to date, we have obtained the following findings.

(1) In the case of $BaSnO_3$, $CaSnO_3$ or $SrSnO_3$ which is free of segregation, the characteristics of the sensor are in close relation with the acid-base property of the surface of the compound. Remarkably improved characteristics can be obtained when the surfaces of particles of $BaSnO_3$ or the like are adapted to have an acid-base strength of greater than 6.8 as determined with Hammett's indicator in benzene.

(2) In the case of $BaSnO_3$, $CaSnO_3$ or $SrSnO_3$, the surfaces of particles become acidic owing to the presence of Si and B as impurities. Generally, Si is present in an amount of about 1000 mol ppm, and B about 500 mol ppm. If the combined amount of Si and B present is about 50 mol ppm, remarkably improved sensor characteristics will result. Accordingly, it is desired to reduce the combined content of Si and B to not higher than 300 mol ppm, more preferably not higher than 200 mol ppm. With respect to each of Si and B, it is desired to reduce the Si content to not higher than 200 mol ppm, and the B content to not higher than 100 mol ppm. $BaSnO_3$ and the like contain as other impurities about 50 to about 1000 mol ppm of Al (1.5 in Pauling electronegativity) and about 50 to about 200 mol ppm of Fe (1.8 in Pauling electronegativity). These impurities are introduced into the compound from the starting material, the water used for the reaction, the reactor, the baking container or the like. The influence of Al or Fe has not been found yet. (3) When a basic element up to 1.3 in Pauling electronegativity is added to $BaSnO_3$ or like compound containing Si and B, the influence of Si and B can be removed. This effect becomes remarkably pronounced by adding the element in an amount of at least ¼, preferably at least ½, of the combined amount of Si and B present in gram atom units. For example, the above-mentioned acid-base strength increases beyond 6.8 when 500 mol ppm of Mg is added to $ASnO_3$ (wherein A is Ba, Ca or Sr) containing a little over 1500 mol ppm of Si and B in combined amount, whereas with addition of 300 mol ppm of Mg, the acid-base strength is not greater than 4.8.

(4) Comparable results can be achieved by giving enhanced basicity to $BaSnO_3$ or the like, by removing the impurities such as Si and B, or by adding a basic element in an amount sufficient to eliminate the influence of Si and B. More specifically, these methods make it possible 1) to inhibit variations in the sensor resistance, 2) to improve the speed of response to changes in the ambient atmosphere at low temperatures, 3) to improve the durability of sensor against various atmospheres, and 4) to inhibit Sn element from diffusing from $BaSnO_3$ or the like into the electrodes used in the sensor. Examples of elements up to 1.3 in electronegativity are Mg, Ca, Sr, Ba, La, Sc, Y and Li, among which Mg and Ca are especially preferable.

(5) It is most desirable to remove Si and B elements from $ASnO_3$ and positively add to $ASnO_3$ an element, such as Mg or Ca, up to 1.3 in electronegativity. This prevents diffusion of Sn into the electrodes more completely than when Si and B are merely removed. In this case, it is desired to reduce the combined amount of Si and B to not greater than 300 mol ppm per mol of $ASnO_3$ and to add 0.05 to 0.5 mol % of Mg or Ca per mol of $ASnO_3$. An excess of Mg or Ca, especially not less than 1 mol % of Mg or Ca, if present, is likely to react with $ASnO_3$ to form $Mg_2SnO_4$ or the like. Addition of 0.05 mol % of Mg is fully effective for eliminating the influence of 1500 mol ppm of Si and B. Preferably, therefore, the lower limit of amount of Mg or the like to be used is 0.05 mol %. Unless Si and B are removed, $ASnO_3$ contains a little over 1500 mol ppm of Si and B in combined amount. When Si and B are positively removed, the combined amount of these elements can be decreased to about 50 mol ppm. The difference between 1500 mol ppm and 50 mol ppm in the combined Si and B content results in a striking difference in the sensor characteristics. Accordingly, the combined content of Si and B is to be decreased preferably to not higher than 300 mol ppm, more preferably to not higher than 200 mol ppm.

(6) Si and B are incorporated into $ASnO_3$ during precipitation of hydrous crystals thereof from the glass container used. Si and B are also introduced into $ASnO_3$, for example, from $BaCl_2$ or $SnCl_4$, the starting material for $ASnO_3$, or from the water used as a reaction solvent.

To prevent the contamination with Si and B, therefore, it is required to use a container having an inner surface made of an Si- and B-free material. Examples of such containers include containers made of high-purity alumina, those made of polypropylene, polyethylene or fluorocarbon resin, and metal containers lined with fluorocarbon resin, polypropylene, polyethylene or like synthetic resin, especially with fluorocarbon resin. When hydrous $ASnO_3$ crystals are to be precipitated, the reaction must be conducted under conditions free from carbon dioxide. A hermetic container is necessary for this purpose. It is difficult to make a hermetic container from alumina because this material is difficult to machine in a comlex fashion. Since the reaction to precipitate hydrous crystals of $ASnO_3$ uses a strongly alkaline solution, the container portion to be exposed to the solutions to be reacted should preferably be made from fluorocarbon resin which is highly resistant to corrosion. Nevertheless, it is difficult to make a large tough container from fluorocarbon resin only. Accordingly, a metal container such as a stainless steel container is especially desirable which is lined with corrosion-resistant fluorocarbon resin. Polypropylene, polyethylene or like synthetic resin is of course usable for lining the container.

To preclude contamination with Si and B from the starting material such as $BaCl_2$ or $SnCl_4$, the starting material to be used should be of high purity. The water or like reaction solvent to be used should also have the highest possible purity. For example, ion-exchanged water, distilled water or the like is to be used as high-purity water.

(7) It is possible to prepare not only $ASnO_3$ but also other perovskite compounds or precursors thereof by a liquid-phase reaction. This reaction gives microscopically uniform perovskite compounds unlike the usual process wherein powders are mixed together and baked. For example, when Sr hydroxide sol and $TiO_2$ sol are dispersed in water and then aged hermetically at a temperature of about 200° C., the sols react with each other to give a sol resembling $SrTiO_3$ in composition. When subjected to thermal decomposition, this sol affords $SrTiO_3$. Similarly, La hydroxide and Co oxide sols, when reacted hermetically in water at a high temperature, give a precursor of $LaCoO_3$.

In these cases, the contamination of the product with impurities from the container is avoidable also by the same method as above, i.e., by making the container from stainless steel or like metal and lining the container with a synthetic resin, especially with corrosion-resistant fluorocarbon resin.

Exhaust gas sensors fulfilling the foregoing requirements can be prepared, for example, by the following process. Sn ions are reacted with ions of at least one member selected from the group consisting of Ca, Sr, Ba and Ra in an alkali solution under a condition free from carbon dioxide, Si ion and B ion to precipitate hydrous crystals of a compound $ASnO_3$ using a reactor having an inner surface formed by an Si- and B-free material such as fluorocarbon resin to avoid contamination of the precipitate with Si and B from the container. The precipitated hydrous crystals of $ASnO_3$ are thermally decomposed to $ASnO_3$, which is then sintered with at least one pair of electrodes connected thereto to obtain a gas sensor member. An element such as Mg or Ca is added to the hydrous crystals before the thermal decomposition or to the $ASnO_3$ resulting from the thermal decomposition. The gas sensor member is caused to be supported by a heat-resistance insulating support member. The gas sensor member, when in the form of a film, is to be obtained as fixed to the support member when the $ASnO_3$ is baked.

BRIEF DESCRIPTION OF THE DRAWINGS

FIGS. 3 to 9 are characteristics diagrams showing distributions of resistance values of exhaust gas sensors;

FIGS. 14 to 19 are characteristics diagrams showing the durability of exhaust gas sensors against a reducing atmosphere at a high temperature;

FIGS. 20 (A), (B) to FIGS. 23 (A), (B) are elementary analysis photographs showing Sn solid solutions formed in exhaust gas sensor electrodes, each FIG. (A) showing a Pt element distribution and each FIG. (B) showing an Sn element distribution;

FIGS. 20 (A), (B) show the result achieved by an exhaust gas sensor reduced to about 50 mol ppm in the combined amount of Si and B;

FIGS. 21 (A), (B) show the result achieved by an exhaust gas sensor reduced to about 50 mol ppm in the combined amount of Si and B;

FIGS. 22 (A), (B) show the result achieved by an exhaust gas sensor having 2000 mol ppm of Si added thereto; and FIGS. 23 (A), (B) show the result achieved by an exhaust gas sensor having 2000 mol ppm of B added thereto.

EMBODIMENTS

Preparation of $BaSnO_3$, 1

Hydrous crystals of $BaSnO_3$ were precipitated in an $N_2$ stream under a $CO_2$-free condition using a borosilicate glass container, which was hermetic to prevent introduction of $CO_2$ from air. $CO_2$, if present, produced $BaCO_3$ in the precipitate.

An aqueous solution of $SnCl_4$ (reagent special grade) was maintained at a pH of at least 13 with sodium hydroxide to obtain a stannic acid solution, to which an aqueous solution of barium chloride (reagent special grade) to precipitate $BaSnO_3 \cdot 7H_2O$ crytals at room temperature. The water used was ion-exchanged water prepared by removing cations such as Si and B by ion exchange. The atomic absorption method was employed for controlling the purity of the $SnCl_4$, $BaCl_2$ and ion-exhanged water to prevent introduction of Si and B therefrom into the precipitate. The water in the reactor was discarded, the precipitate was filtered off, pure water (i.e. ion-exchanged water, the same as hereinafter) was added thereto, and the mixture was heated to at least 55° C. The $BaSnO_3 \cdot 7H_2O$ was decomposed to produce $BaSnO_3 \cdot 5H_2O$ precipitate. The mother liquid was discarded, the precipitate was filtered off and pure water was added thereto again at an elevated temperature of at least 70° C. The crystals of $BaSn \cdot 5H_2O$ decomposed, giving $BaSnO_3 \cdot 3H_2O$ crystals as precipitated. The crystals were about tens of micrometers in length, needlelike, colorless and transparent. The precipitate was filtered off to collect the crystals of $BaSnO_3 \cdot 3H_2O$.

The solvent is useful insofar as it is an aqueous solvent consisting predominantly of water. pH of the system is such that stannic acid will not precipitate. Any desired alkali is usable. Washing with water is repeated starting with $BaSnO_3 7H_2O$ to remove Na ions and like impurities. The product $BaSnO_3 \cdot 3H_2O$ is a 1:1 compound of Ba and Sn. Since the Ba and Sn are microscopically uniform, the compound, when thermally decomposed, gives $BaSnO_3$ which is 1 in Ba/Sn ratio and in which Ba and Sn are distributed microscopically uniformly.

When calcium chloride is used in place of barium chloride, hydrous crystals of $CaSnO_3$ separate out, while use of strontium chloride affords hydrous crystals of $SrSnO_3$ as a precipitate.

MgO or CaO was added to the collected $BaSnO_3 \cdot 3H_2O$ collected. These crystals are likely to decompose or degrade on contact with carbonate ions. Since water easily dissolves carbon dioxide, a solution or dispersion of Mg or Ca compound in a nonaqueous solvent was used for the addition of Mg or Ca. In the present experiment, ethanol was used as the nonaqueous solvent. It is desirable to use an organic nonaqueous solvent as the nonaqueous solvent. When $MgCl_2$ or $CaCl2$ is used as the additive, the $BaSnO_3 \cdot 3H_2O$ was impregnated with an ethanol solution of the compound. When MgO was used, finely divided MgO was ultrasonically dispersed in ethanol for use in impregnation. Mg ethylate, when to be used, was dissolved in ethanol for use in impregnation. As a rule, the additive was used in an amount of 0.2 mol % per mol of $BaSnO_3$. The additive was used in the range of 0.03 to 1 mol % for experiment. Mg- or Ca-free crystals were used for the following reference examples, and crystals with Mg or Ca added thereto for the examples of the invention given below. One mol % refers to the addition of 0.01 mol per mol of $ASnO_3$.

After the addition of Mg or Ca, the $BaSnO_3 \cdot 3H_2O$ crystals were thermally decomposed to $BaSnO_3$ in air using alumina of high purity for the boat. The thermal decomposition was conducted at 1400° C. for 8 hours. The crystals start to decompose at about 600° C. Preferably, the thermal decomposition is conducted at 800° to 1500° C. for about 1 to about 20 hours. On thermal decomposition, $BaSnO_3 \cdot 3H_2O$ is converted to $BaSnO_3$ crystals adhering to one another and retaining the appearance of $BaSnO_3 \cdot 3H_2O$ particles (needlelike crystals tens of micrometers in length) The Mg or Ca added changes to MgO or CaO.

The $BaSnO_3$ resulting from thermal decomposition was filled into a die without pulverization and press-formed at a pressure of 5 tons/$cm^2$ into a chip having a pair of electrodes embedded therein. Pulverization can be dispensed with because the needlelike $BaSnO_3$ particles are freely flowable and can be easily filled into the die uniformly. Used as the electrodes was a Pt wire (60 micrometers in diameter) having about 0.05 to about 0.1 wt. % of $ZrO_2$ added thereto at the grain boundary. This electrode wire is highly durable and less prone to deterioration due to the diffusion of Sn through BaSnO$_3$ especially in reducing atmospheres at high temperatures (Unexamined Japanese Patent Publication SHO 62-14,047, U.S. patent application Ser. No. 883,130). The press-formed chip was placed into a high-purity alumina container and heated in air at 1450° C. for 4 hours for sintering to obtain a gas sensor member. Preferably, the chip is baked at a temperature not lower than the thermal decomposition temperature of hydrous crystals of BaSnO$_3$, more preferably at 1200° to 1600° C., for 1 to 20 hours.

MgO or CaO is added to eliminate the influence of Si and B impurities because if the precipitation reaction to give the hydrous crystals of BaSnO$_3$ is conducted in a strong alkali, Si and B dissolve out from the borosilicate glass of the container into BaSnO$_3$. The additive element Mg or Ca may be replaced by Sr, Ba or Ra of the same group. As will be described later, the effect of Mg or Ca is attributable to the modification of the acid-base property of the surface of the BaSnO$_3$. Accordingly, the electronegativity of the element to be added is of importance and should be up to 1.3 in terms of Pauling electronegativity. Such elements include, besides alkaline earth elements, La and Sc. MgO, CaO or the like can be added at any desired time. For example, an Mg or Ca containing compound may be added to BaSnO$_3$ after the thermal decomposition of BaSnO$_3$·3H$_2$O and converted to MgO or CaO on sintering after press forming.

Preparation of BaSnO$_3$, 2

BaSnO$_3$ crystals were prepared by the same precipitation reaction as above using a polypropylene container to prevent introduction of Si and B, then pressformed and sintered to obtain the same gas sensor member as above in the form of a chip. This experiment was carried out under exactly the same conditions as in the foregoing example wherein the borosilicate glass container was used. Since the precipitation reaction was conducted in a strong alkali, the polypropylene container deteriorated when used for preparing hydrous crystals of BaSnO$_3$ several times. It is therefore desirable that the inner surface of the container be formed by fluorocarbon resin. In view of the overall strength of the container, it is more desirable to use a container of stainless steel or like metal lined with fluorocarbon resin.

Analysis of BaSnO$_3$

The impurities in the BaSnO$_3$ resulting from the thermal decomposition of BaSn$_3$·3H$_2$O were analyzed. All the samples of BaSnO$_3$ thus obtained were found to be free from Ba and Sn segregates. The segregation can be detected by local elementary analysis of BaSnO$_3$ or by Fourier transform IR spectroscopy of this compound from CO$_3$ ion absorption peak at around 1400 cm$^{-1}$. In BaSnO$_3$, Ba and Sn are in a microscopically uneven distribution. Such BaSnO$_3$ exhibits a CO$_3$ ion absorption peak at around 1400$^{-1}$. All the lots obtained with use of the glass container were found to contain a little over 1000 mol ppm of Si per mol of BaSnO$_3$ and about 500 mol ppm (i.e., mol ppm per mol of BaSnO$_3$, the same as hereinafter) of B. with those obtained with use of the polypropylene container, the Si content was up to 50 mol ppm, while B was undetectable. However, even with use of the polypropylene container, some samples contained about 300 to about 400 mol ppm of Si introduced from ion-exchanged water. When the polypropylene container is used, it is desirable to control the combined content of Si and B to not higher than 300 mol ppm per mol of ASnO$_3$ and to add 500 to 5000 mol ppm of Mg or Ca per mol of ASnO$_3$.

The lots of BaSnO$_3$ prepared by the experiments were chiefly three kinds: BS10 and BS13 representing BaSnO$_3$ obtained with use of the glass container, and BS15 standing for BaSnO$_3$ obtained with use of the polypropylene container. Besides these, another lot was also prepared under exactly the same conditions as BS15, i.e., BS16 (up to 50 mol ppm of Si with undetectable B).

The surface acid-base property of BaSnO$_3$ particles obtained by the thermal decomposition of BaSnO$_3$·3H$_2$O was determined from the color reactions of four kinds of Hammett's indicators, i.e., Dimethyl Yellow, Methyl Red, Neutral Red, phenolphthalein, using benzene solvent. More specifically, BaSnO$_3$ was pretreated in dry air at 700° C. to remove hydroxy goups, etc. from the surface, allowd to stand in a desiccator, and then added in an amount of about 200 mg to 2 ml of anhydrous benzene. Hammett's indicator was added to this sample, and the acid-base strength was determined from the color of BaSnO$_3$ developed. Table 1 shows the acid-base strength (Hammett's function Ho unit) thus determined. The symbols representing the strength values in the table stand for the following:

A: $3.3 < \text{Ho} \leq 4.8$
B: $4.8 < \text{Ho} \leq 6.8$
C: $6.8 < \text{Ho} \leq 9.3$
D: $9.3 < \text{Ho}$ The lot BS15 with SiO$_2$ added thereto was prepared by impregnating BaSnO$_3$·3H$_2$O with a dispersion of finely divided SiO$_2$ in ethanol to thereby intentionally add SiO$_2$ to the compound. The amount of additive used as expressed in mol % is per mol of BaSnO$_3$ (the same as hereinafter).

The acid-base strength thus determined differs from the pH of a dispersion of the same BaSnO$_3$ sample in water. For example, the Mg-free BaSnO$_3$ represented by BS10 has a strength value of A as listed in Table 1, whereas when the BaSnO$_3$ is dispersed in water in 10 times the amount by weight of the compound, then stirred and thereafter allowed to stand for 1 hour, the resulting supernatant exhibits a pH of 8. The difference between the result achieved by Hammett's indicator and the result obtained by pH measurement is attributable to the following reason. The pH value strongly reflects the influence of the hydroxyl on the surface of BaSnO$_3$, whereas the value obtained by Hammette indicator reflects the property of the BaSnO$_3$ as a solid acid, solid vase, Lewis acid or Lewis base.

TABLE 1

| Lot | Acid-Base Strength |
|---|---|
| | Acid-base strength |
| BS10 free from Mg | A |
| BS10 with 0.2 mol % MgCl$_2$ | C |
| BS13 free from Mg | A |
| BS13 with 0.03 mol % MgO | A |
| BS13 with 0.2 mol % MgO | C |
| BS13 with 0.05 mol % MgCl$_2$ | C |
| BS13 with 0.2 mol % MgCl$_2$ | C |
| BS13 with 1.0 mol % MgCl$_2$ | D |
| BS13 with 0.2 mol % CaCl$_2$ | C |
| BS15 free from Mg | C |
| BS15 with 0.2 mol % SiO$_2$ | A |

TABLE 1-continued

| Lot | Acid-Base Strength<br>Acid-base strength |
|---|---|
| BS15 with 0.2 mol % Mg ethylate | C |

The table reveals the following. The $BaSnO_3$ with a low Si or B content (BS15) has a neutral or basic surface, whereas the lots wherein Si and B are present as introduced from the glass container have an acid surface. The addition of Mg or Ca renders the surface neutral or basic. Conversely, intentional addition of Si or B to the sample with a low Si or B content makes the surface acid.

Addition of Rh

To give improved response characteristics to sensors at low temperatures, an Rh catalyst was added to some samples. The sample as press-formed was caused to support the catalyst by impregnating the sample with an aqueous solution of rhodium chloride, drying the sample and thermally decomposing the same at 95° C. for 3 hours. The Rh was added in an amount of 150 wt. ppm in terms of $Rh/BaSnO_3$ ratio. The term "acid-base strength" of $BaSnO_3$ as used herein refers to the strength thereof before the addition of the Rh or like catalyst. For example, if chlorine remains in the $BaSnO_3$ compound of the invention owing to the addition of Rh, the compound exhibits altered acid-base strength. Rhodium has high electronegativity and therefore alters the acid base strength when added. The significant acid-base strength is a value before the addition of the catalyst.

Construction of Exhaust Gas Sensor

Figure 1:
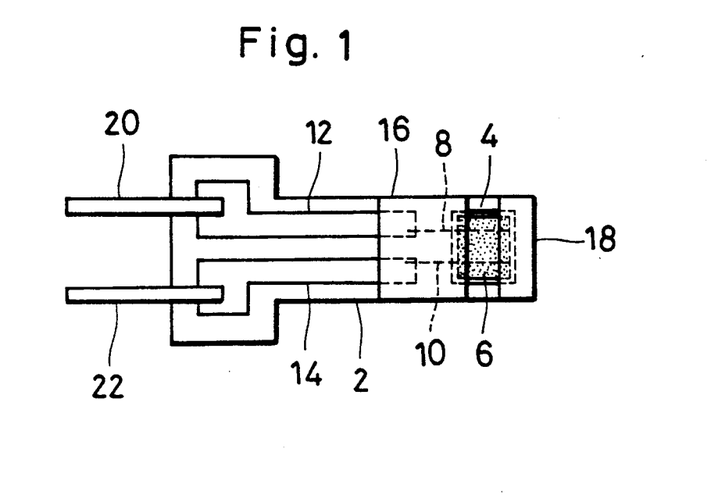
FIG. 1 is a front view showing an exhaust gas sensor.

FIG. 1 shows an exhaust gas sensor fabricated using a baked chip. The sensor shown has an alumina substrate 2, which is formed with a recess 4 having accommodated therein the chip, i.e. gas sensor member 6. Indicated at 8 and 10 are electrodes comprising a Pt wire 60 micrometers in diameter and having about 0.05 to about 0.1 wt. % of $ZrO_2$ separated out at the grain boundary. With the electrodes 8 and 10, the $ZrO_2$ at the grain boundary prevents the Sn element of $BaSnO_3$ from diffusing into the interior of Pt. A pair of printed electrodes 12, 14 are joined to the wire electrodes 8, 10, respectively. Spray coatings 16, 18 of compact structure locally cover the surface of the chip 6 and serve to fix the chip 6 in the recess 4. Indicated at 20, 22 are external leads. The sensor can be of any desired construction.

Influence of Segregation

Segregation exerts a marked influence on the characteristics of sensors. $BaSnO_3$ with segregation has a distribution of Ba or Sn element within the crystals of the compound. Sensors employing $BaSnO_3$ involving segregation are low in oxygen sensitivity and in the accuracy with which the composition of exhaust gases is detectable. They are low also in the speed of response to changes in the ambient atmosphere. When such a sensor is used as installed in the exhaust pipe from a motor vehicle engine, $BaSnO_3$ decomposes upon reacting with P in the exhaust gas. $BaSnO_3$ with segregation contains BaO and like components, is originally alkaline, is unaffected with traces of impurities such as Si and B, and accordingly need not be controlled in surface acid-base property, which on the other hand is not controllable with a small amount of additive. Furthermore, $BaSnO_3$ involving segregation deteriorates through condensation of water and contact with $SO_2$ and like poisons.

Figure 2:
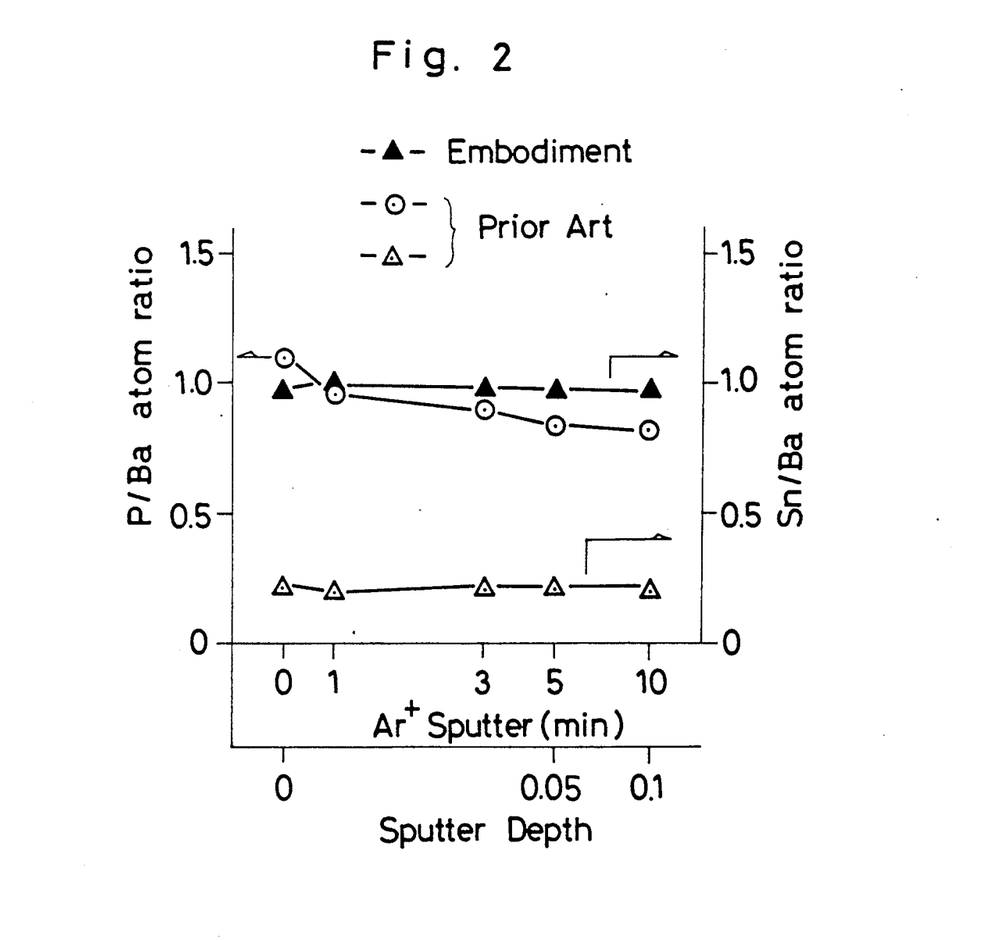
FIG. 2 is a characteristics diagram showing diffusion of P element into $BaSnO_3$ and decomposition of $BaSnO_3$ to demonstrate the difference resulting from segregation.

As a reference example relating to $BaSnO_3$ with segregation, $BaCO_3$ and $SnO_2$ were reacted in air at 1200° C. for 4 hours to obtain $BaSnO_3$, which was then pulverized for 2 hours, press-formed and thereafter sintered at 1300° C. for 4 hours to obtain a sensor of the construction shown in FIG. 1. Ba and Sn segregates are present in the $BaSnO_3$ of the reference example. The sensor with this $BaSnO_3$ and a sensor incorporating the lot BS10 (free from Mg) were used and checked for durability with the result shown in FIG. 2. Each sensor was installed in the exhaust pipe of the engine of a motor vehicle, which was driven for one hour daily for one week. The chip 6 was thereafter surface-etched by sputtering with Ar ions and checked for composition at varying depths from the surface. With the $BaSnO_3$ involving segregation, Sn is lost in the vicinity of the surface with an accumulation of P, whereas with the compound free of segregation, the Sn concentration remains constant regardless of the depth with no accumulation of P.

The thermal decomposition of hydrous crystals of $BaSnO_3$ is the method of preparing segregation-free $BaSnO_3$ most easily. Nevertheless, use of hydrous crystals is not limitative but $BaSnO_3$ prepared by any desired process is usable insofar as it is free of segregation. For example, segregation-free $BaSnO_3$ was obtained by reacting $BaCO_3$ with $SnO_2$ at 1300° C. for 2 hours to obtain $BaSnO_3$, and repeating three times the steps of pulverizing the compound for 2 hours and baking the product at 1300° C. for 2 hours. When press-formed and sintered in the same manner as above, this $BaSnO_3$ affords the same sensor as the one according to the invention. The $BaSnO_3$, which is free from segregates, is sensitive to Si and B. Accordingly, Mg, Ca or the like may be added thereto to eliminate the influence of Si or B.

Variations in Sensor Resistance

Each of FIGS. 3 to 9 shows a distribution of resistance values of sensors prepared using a particular lot. The resistance value means that of the sensor measured in air at 800° C. immediately after the fabrication thereof. In each diagram, plotted as abscissa is the resistance value vs. the frequency of distribution as expressed in the number of sensors as ordinate. Table 2 shows the samples used.

TABLE 2

Figure 3:
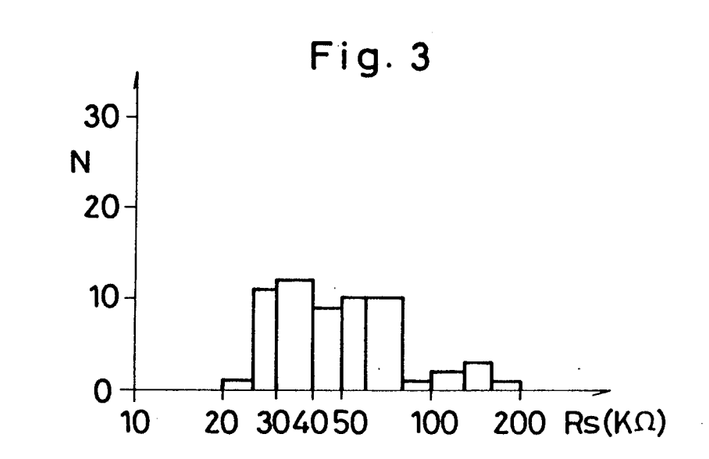
FIGS. 3 and 4 each show the distribution of resistance values of conventional exhaust gas sensors containing Si and B in a combined amount of about 1500 mol ppm.
Figure 4:
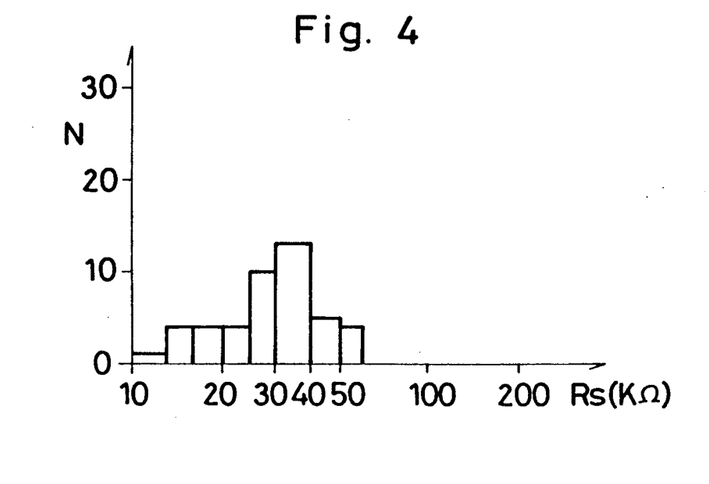
Figure 5:
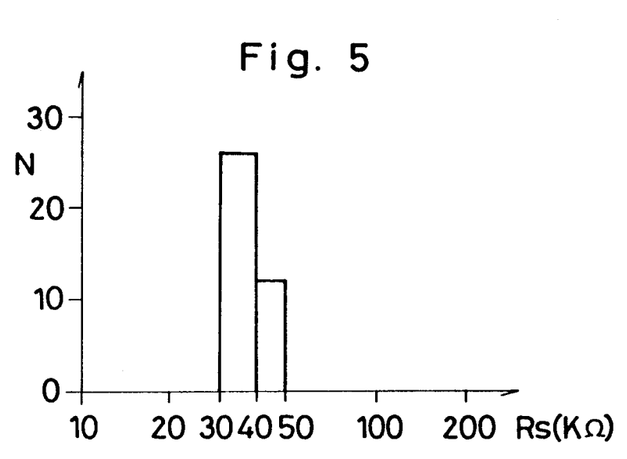
FIGS. 5 to 7 each show the distribution of resistance values of exhaust gas sensors containing Si and B in a combined amount of about 1500 mol ppm and having 2000 mol ppm of Mg added thereto.
Figure 6:
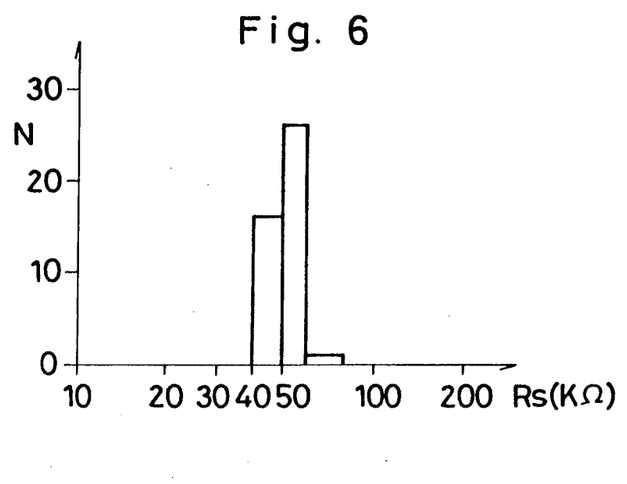
Figure 7:
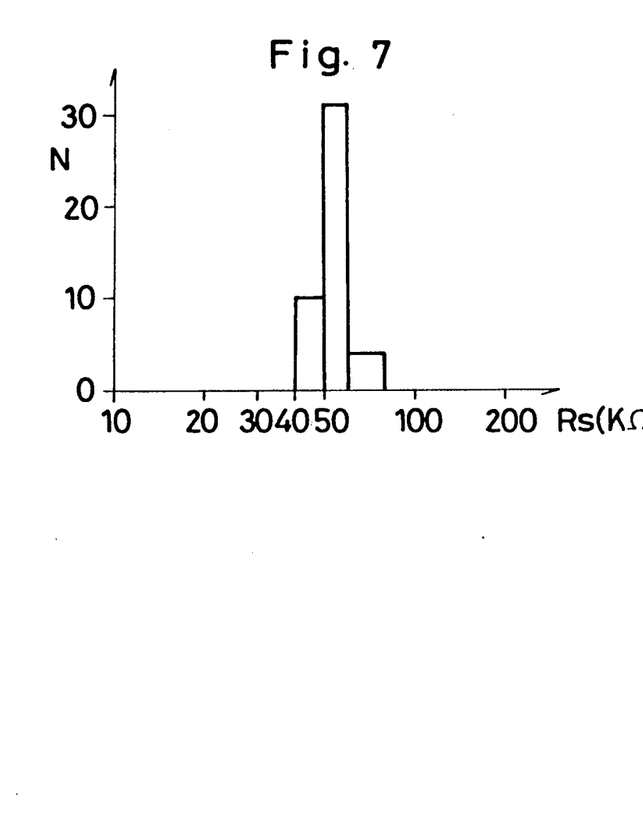
Figure 8:
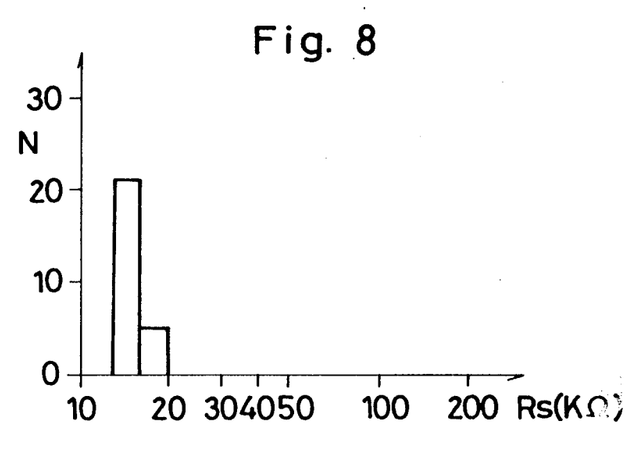
FIG. 8 shows the distribution of resistance values of exhaust gas sensors decreased to about 50 mol ppm in the combined amount of Si and B.
Figure 9:
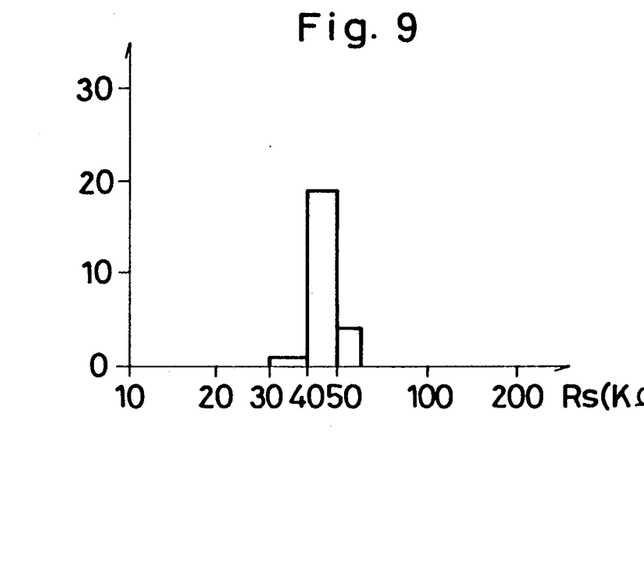
FIG. 9 shows the distribution of resistance values of exhaust gas sensors reduced to about 50 mol ppm in the combined amount of Si and B and having 2000 mol ppm of Mg added thereto.

| FIG. | FIGS. 3 to 9<br>Sample |
|---|---|
| FIG. 3 | BS10 free from $MgCl_2$ or the like |
| FIG. 4 | BS13 free from $MgCl_2$ or the like |
| FIG. 5 | BS10 with 0.2 mol % $MgCl_2$ |
| FIG. 6 | BS13 with 0.2 mol % $MgCl_2$ |
| FIG. 7 | BS13 with 0.2 mol % MgO |
| FIG. 8 | BS15 free from $MgCl_2$ or the like |
| FIG. 9 | BS15 with 0.2 mol % Mg ethylate |

With the sample with addition of MgO or $MgCl_2$, or with the sample wherein $BaSnO_3$ has a neutral or basic surface, variations in sensor resistance are small. The sample with a low Si or B content is also small in variations. In contrast, the sample having an acid surface or containing Si or B varies greatly in resistance. Table 3 shows variations in sensor resistance determined for other samples not shown. The result is expressed in the range of 10% to 90% distribution of resistance values of 20 to 30 sensors. The resistance value was measured in the same manner as is the case with FIGS. 3 to 9.

TABLE 3

| Lot | Variations in Resistance value<br>Distribution range of resistance values (kΩ) |
|---|---|
| BS13 with 0.03 mol % MgO | 25-60 |
| BS13 with 0.05 mol % MgCl$_2$ | 30-50 |
| BS13 with 0.2 mol % CaCl$_2$ | 40-60 |
| BS15 with 0.2 mol % SiO$_2$ | 30-100 |

Speed of Response

As is well known, the speed of response of sensors to changes in atmosphere is high at high temperatures but low at low temperatures. Examples of the invention and reference examples are comparable in the speed of response. The speed of response was measured by the following method. The atmosphere was changed over between 1.02 to 0.98 in λ (equivalent ratio of the exhaust gas) at a time interval of 20 seconds, and the sensor resistance was checked for response to the change. The time for 10% to 90% response was measured as the speed of response.

The speed of response at a high temperature (800° C.) to the change from lean L (above 1 in λ) to rich R (below 1 in λ) was about 0.13 to about 0.2 second for any example, and about 0.1 to about 0.2 second for any reference example. The speed of response to the change from rich R to lean L was about 0.1 to about 0.2 second, and about 0.14 to about 0.21 second for any reference example. The Rh catalyst added contributed almost nothing to the response speed at the high temperature.

Figure 10:
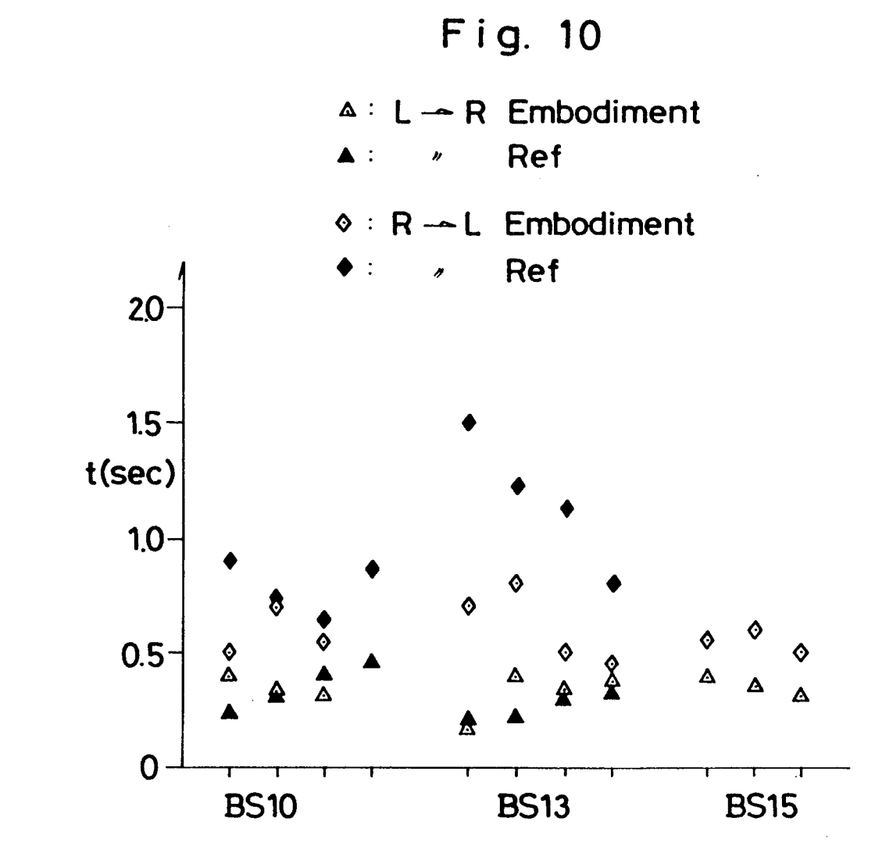
FIG. 10 is a characteristics diagram showing the speed of response of catalyst-free exhaust gas sensors at 500° C.

Rh-free sensors were tested for the speed of response at a low temperature (500° C.) with the results given in FIG. 10. The samples of the reference example had an acid surface and contained Si and B. The samples of the invention are BS10 and BS 13 with addition of 0.2 mol % of MgCl$_2$, and BS15 prepared using the polypropylene container to avoid introduction of Si and B without adding MgCl$_2$ or the like. The reference samples included one varying greatly in response speed and low in response speed, and are therefore lower in response speed than those of the invention on the average.

Figure 11:
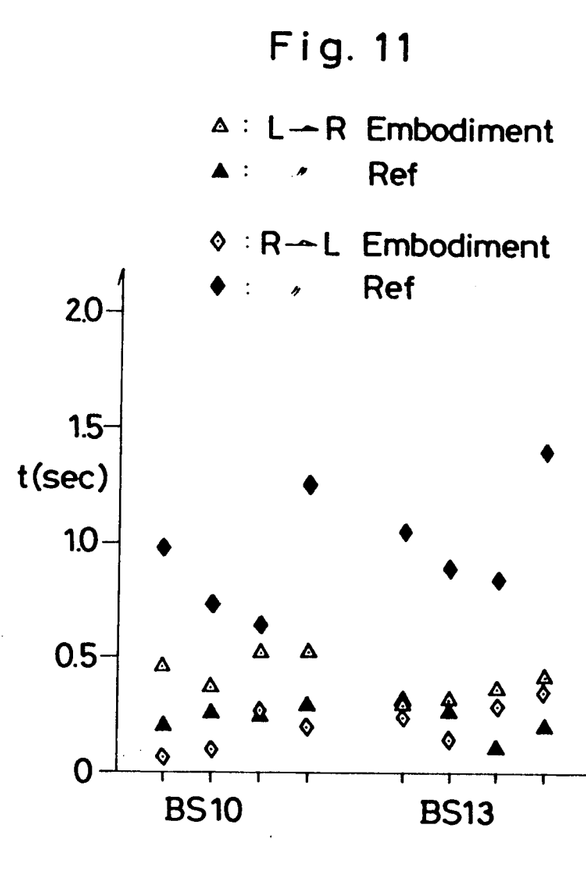
FIG. 11 is a characteristics diagram showing the speed of response of exhaust gas sensors with Rh catalyst at 500° C.

Samples with addition of 150 wt. ppm of Rh catalyst were tested for the speed of response at 500° C., with the results shown in FIG. 11. The symbols representing the samples have the same meaning as in FIG. 10. The reference samples were lower than the samples of the invention in response speed.

Table 4 additionally shows the results achieved by other samples with addition of 150 wt. ppm of Rh when they were tested for the speed of response at 500° C. Each value is the average of four sensors.

TABLE 4

| | Speed of Response | |
|---|---|---|
| Lot | Speed of Response (sec) | |
| | L → R | R → L |
| BS13 with 0.05 ml % MgCl$_2$ | 0.4 | 0.2 |
| BS13 with 0.2 mol % CaCl$_2$ | 0.4 | 0.3 |
| BS13 with 1.0 mol % MgCl$_2$ | 0.4 | 0.2 |

Durability against Various Atmospheres

Figure 12:
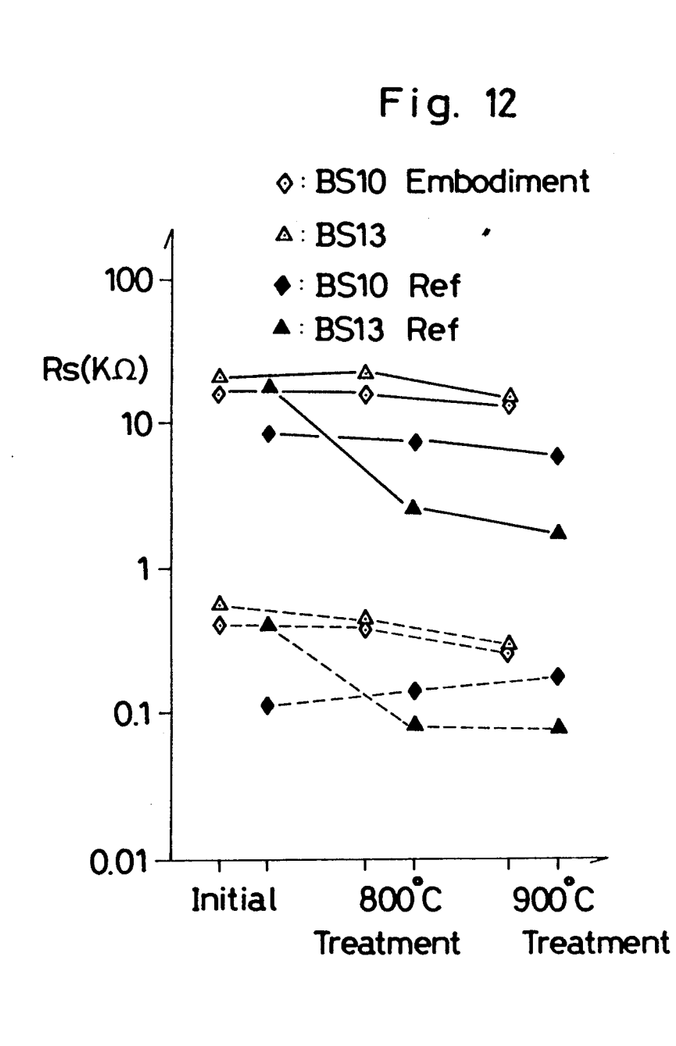
FIG. 12 is a characteristics diagram showing the durability of exhaust gas sensors against $SO_2$ poisoning.

FIG. 12 shows the results obtained by testing sensors for durability against an atmosphere containing 60 vol. ppm of SO$_2$. The atmosphere was prepared by adding 60 vol. ppm of SO$_2$ to an N$_2$-balanced system containing 0.7% O$_2$ and H$_2$O in an amount corresponding to the saturated water vapor pressure at 20°0 C. The sensor was maintained at 800° C. for 3 hours in a stream of this atmosphere, then withdrawn and checked for variations in resistance value and response speed, subsequently exposed to the SO$_2$ atmosphere again at 900° C. for 3 hours, and thereafter checked again for variations in resistance value and response speed. The samples tested contained 150 wt. ppm of Rh and included reference samples BS10 and BS13 free from MgCl$_2$ or the like and samples of the invention BS10 and BS13 treated with 0.2 mol % of MgCl$_2$ as shown in FIG. 12. The solid line in the diagram represents the resistance value in an atmosphere with λ of 1.02 at 850° C., and the broken line represents the resistance value in an atmosphere with λ of 0.98. The sensor becomes poisoned with the SO$_2$ atmosphere when contaminated with Si and B.

Figure 13:
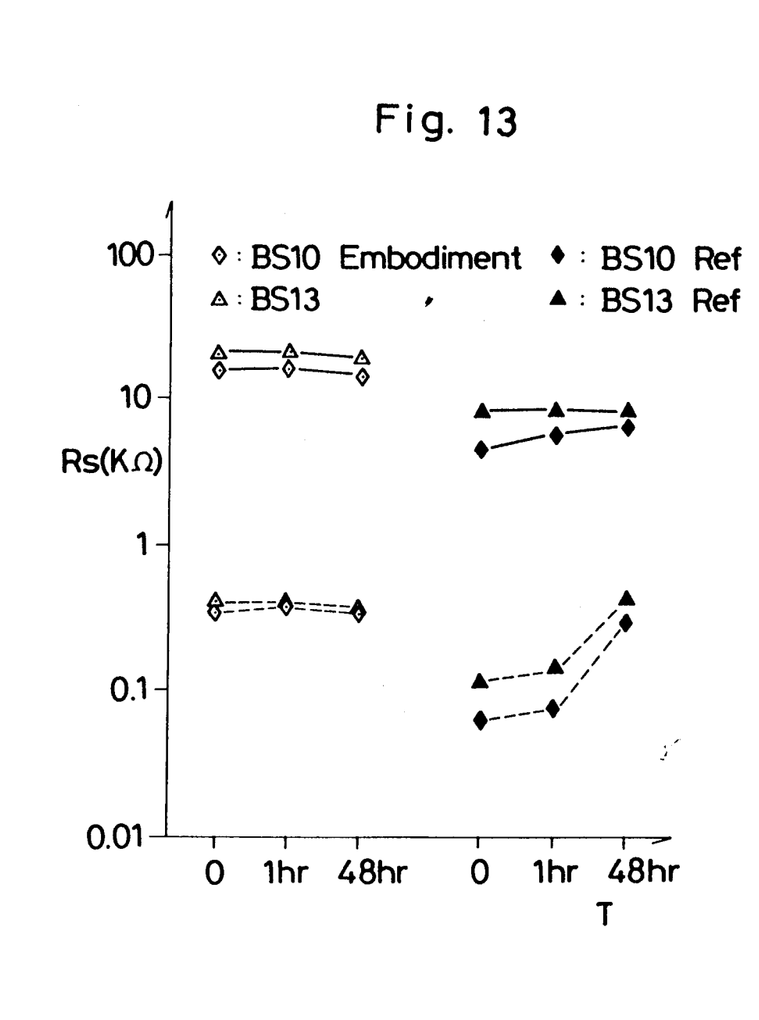
FIG. 13 is a characteristics diagram showing the durability of exhaust gas sensors against an atmosphere involving condensation of water.

FIG. 13 shows results achieved in respect of the durability to an atmosphere involving condensation of water. The samples used and data shown have exactly the same meaning as in FIG. 12; the samples were sensors with addition of 150 wt. ppm of Rh. The sensors were allowed to stand at room temperature in the above atmosphere, i.e., in air at 25° C. and RH 100%, and then checked for variations in the resistance value and response speed. The reference samples exhibited variations in the resistance value.

FIGS. 14 to 19 show the results obtained by testing samples for durability in a strong reducing atmosphere. All the samples had 150 wt. ppm of Rh catalyst added thereto. Table 5 shows the samples.

TABLE 5

Figure 14:
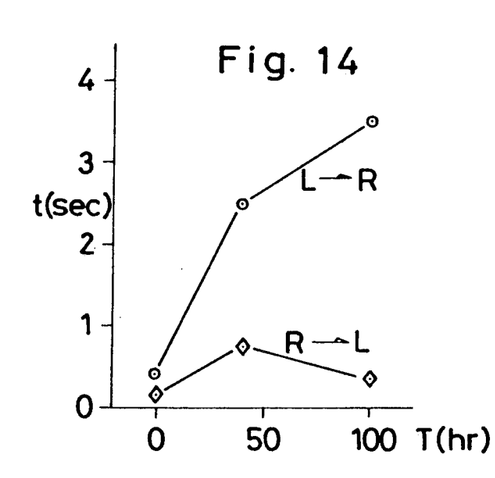
FIGS. 14 and 15 each show the characteristics of an exhaust gas sensor containing Si and B in a combined amount of about 1500 mol ppm.
Figure 15:
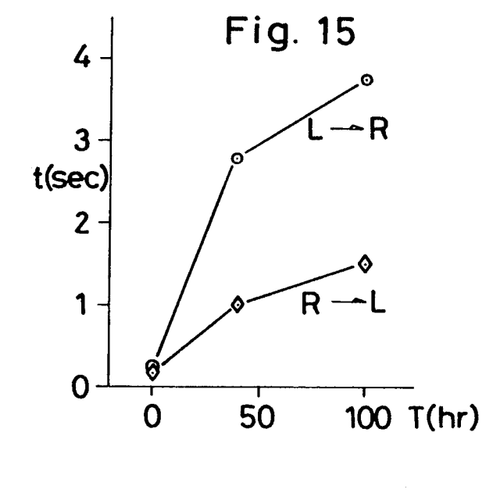
Figure 16:
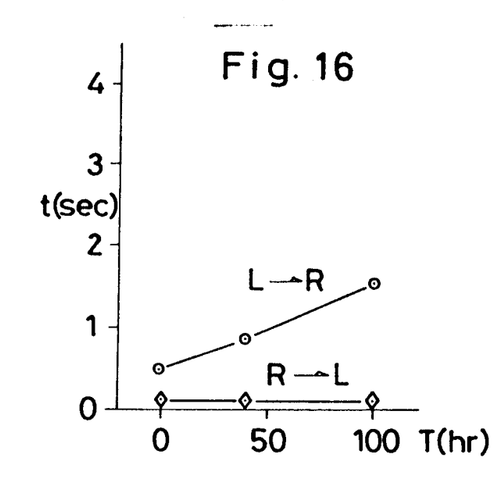
FIGS. 16 and 17 each show the characteristics of an exhaust gas sensor containing Si and B in a combined amount of about 1500 mol ppm and having 2000 mol ppm of Mg added thereto.
Figure 17:
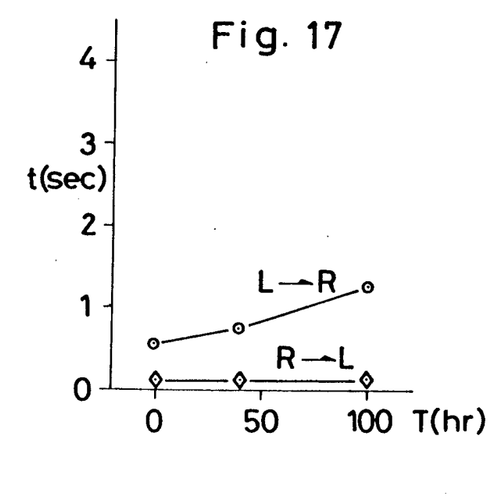
Figure 18:
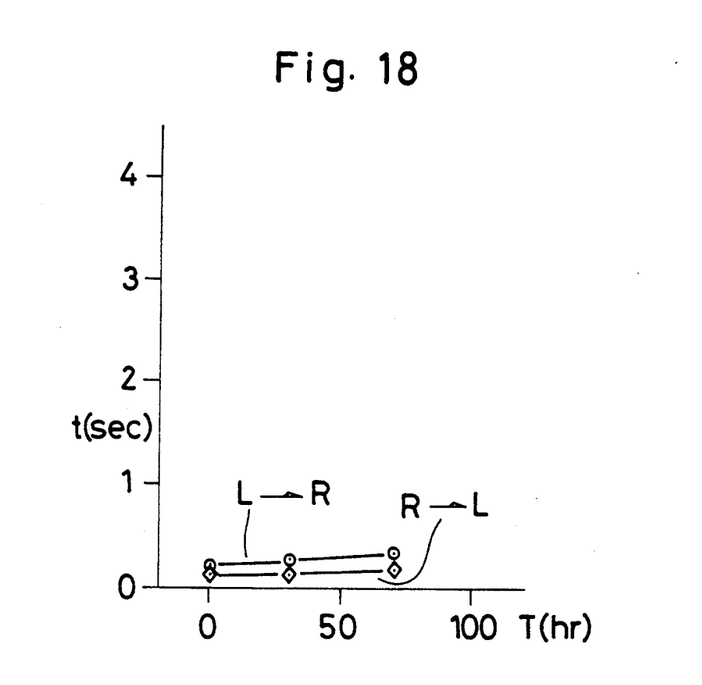
FIG. 18 shows the characteristics of an exhaust gas sensor reduced to about 50 mol ppm in the combined amount of Si and B.
Figure 19:
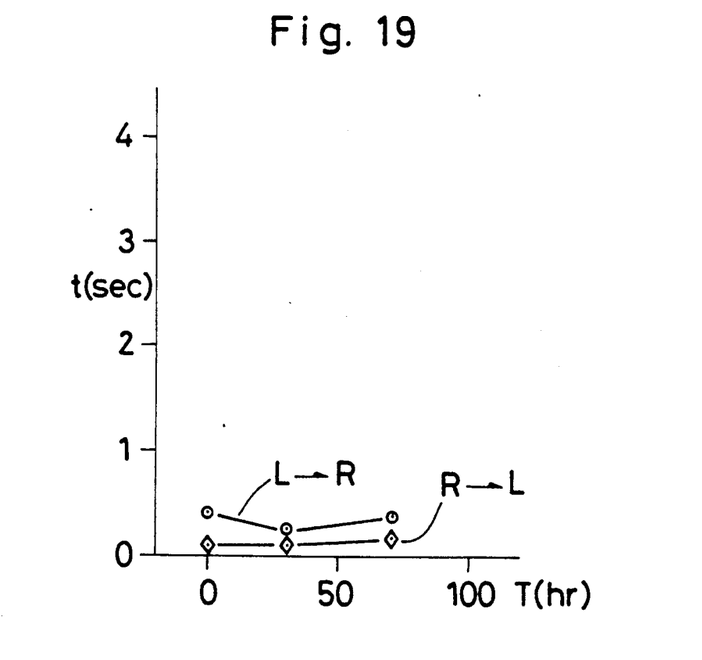
FIG. 19 shows the characteristics of an exhaust gas sensor reduced to about 50 mol ppm in the combined amount of Si and B and having 2000 mol ppm of Mg added thereto.

| FIG. | FIGS. 14 to 19<br>Sample |
|---|---|
| FIG. 14 | BS10 free from MgCl$_2$ or the like |
| FIG. 15 | BS13 free from MgCl$_2$ or the like |
| FIG. 16 | BS10 with 0.2 mol % MgCl$_2$ |
| FIG. 17 | BS13 with 0.2 mol % MgCl$_2$ |
| FIG. 18 | BS15 free from MgCl$_2$ or the like |
| FIG. 19 | BS15 with 0.2 mol % Mg ethylate |

The sensor was held in a strong reducing atmosphere, 0.85 to 0.90 in λ, at 900° C. for 70 to 100 hours, and then checked for variations in the speed of response at 500° C. The presence of Si and B, or the acid-base property of the BaSnO$_3$ surface produces a marked influence on the durability. The durability can be improved by removing Si and B, adding MgCl$_2$ or modifying the surface to basicity.

The durability of the sensor to the three kinds of atmospheres, i.e., SO$_2$- and H$_2$O-containing atmospheres and reducing atmosphere, involved the following tendency. The variation in the resistance value and the reduction in the response speed are not independent of each other. The sensors undergoing variations in the resistance value are lower in the speed of response, while the reduction in the speed of response is accompanied by variations in the resistance value. Sensors other than those not represented in the diagrams concerned also exhibited a similar tendency. More specifically, enhanced durability to the above atmospheres results also from the use of CaCl$_2$ in place of MgCl$_2$, or from the use of a polypropylene container to preclude contamination with Si and B instead of the addition of MgCl$_2$ or CaCl$_2$. Conversely, the durability diminishes when Si is intentionally added to the sample prepared with use of the polypropylene container.

Formation of Sn Solid Solution in Electrodes

Another problem encountered with BaSnO$_3$, SrSnO$_3$ and CaSnO$_3$ is that Sn, which is highly active, diffuses into the electrodes of Pt or the like, forming a solid solution. This phenomenon becomes pronounced in a reducing atmosphere at high temperatures.

Figure 20A:
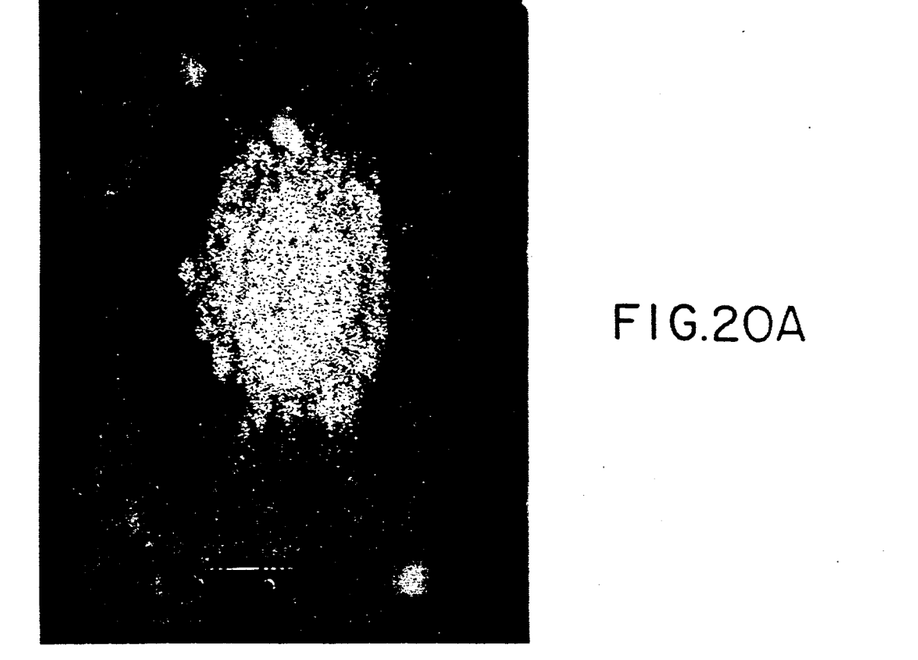
Figure 20B:
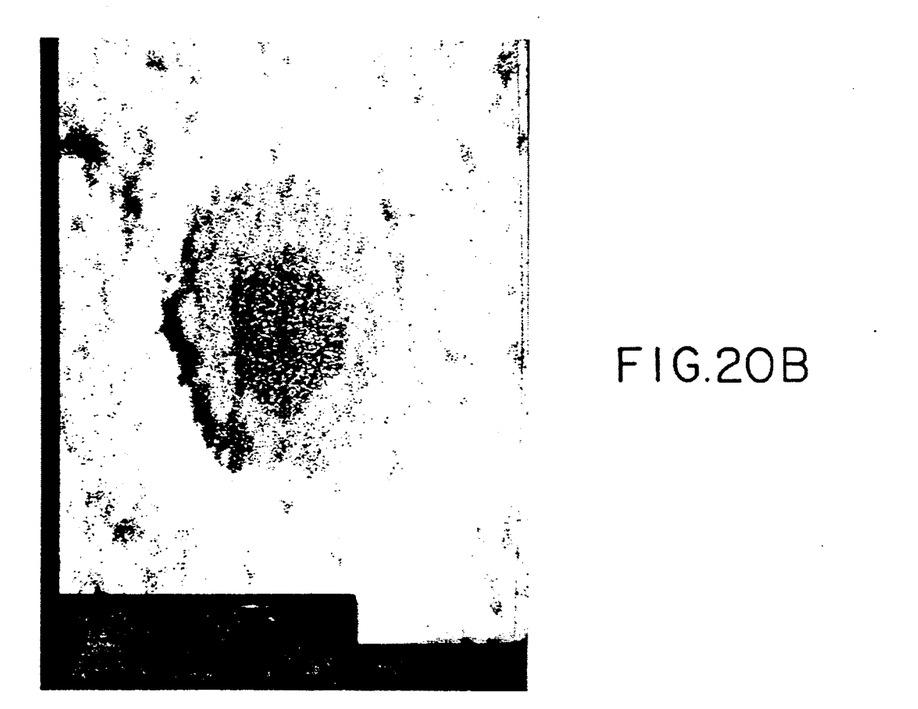
Figure 21A:
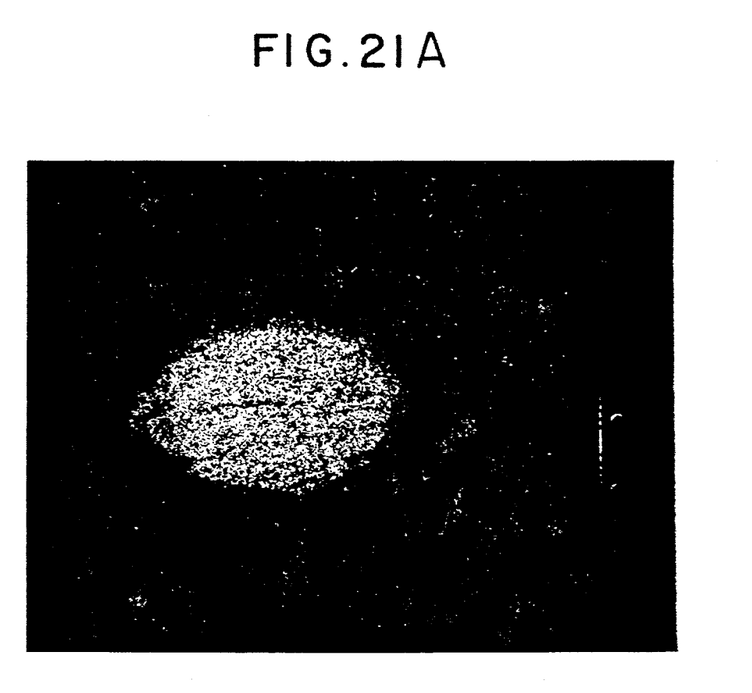
Figure 21B:
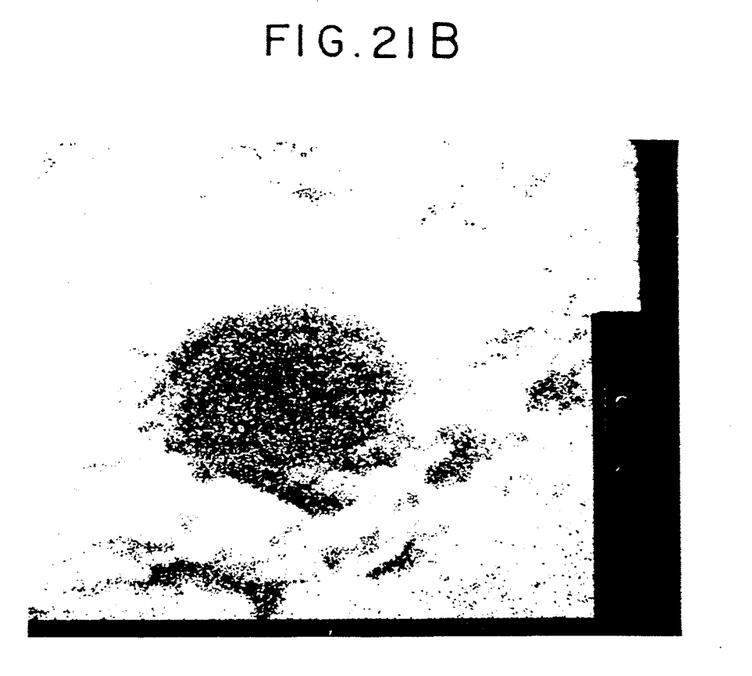
Figure 22A:
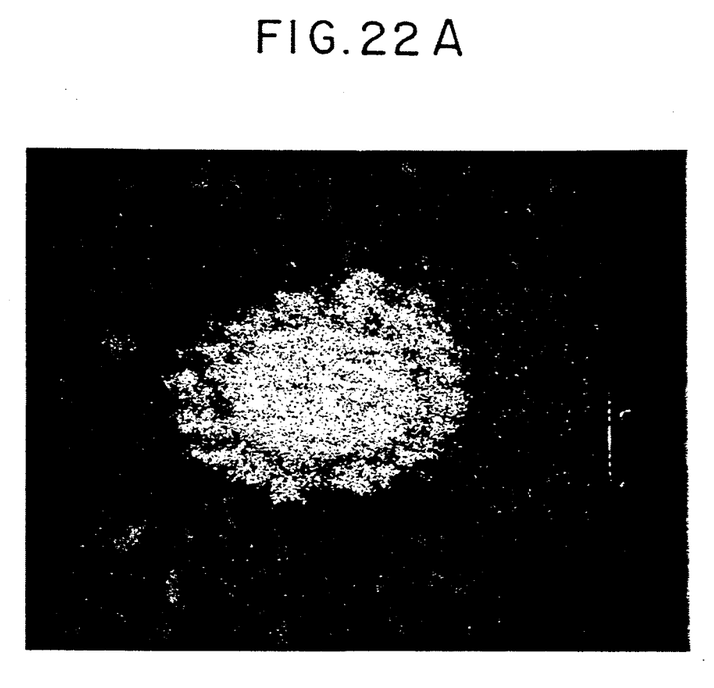
Figure 22B:
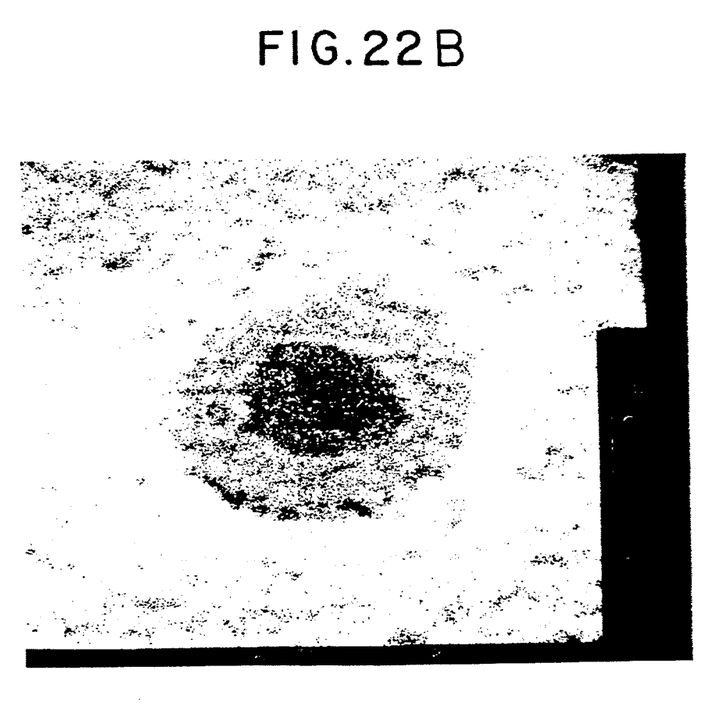
Figure 23A:
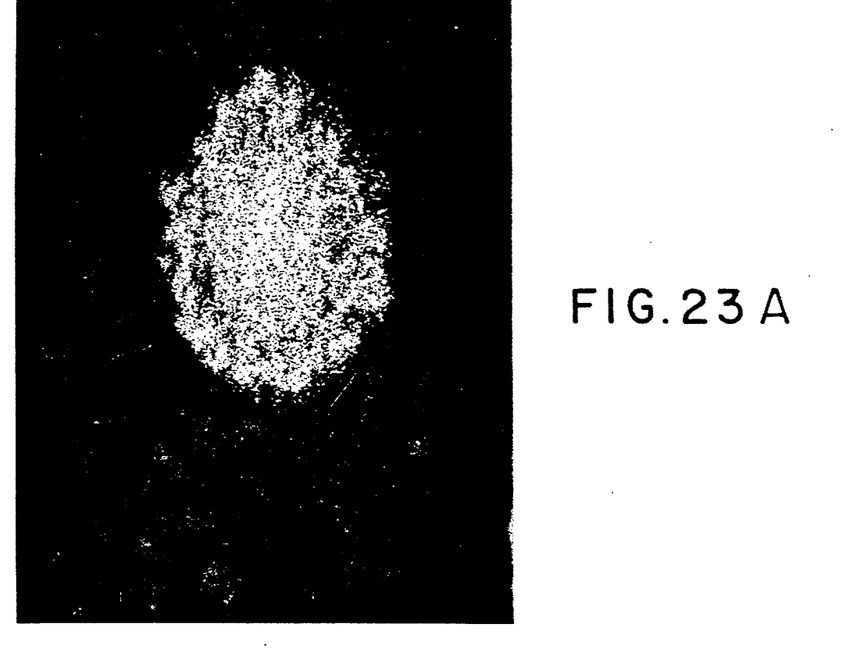
Figure 23B:
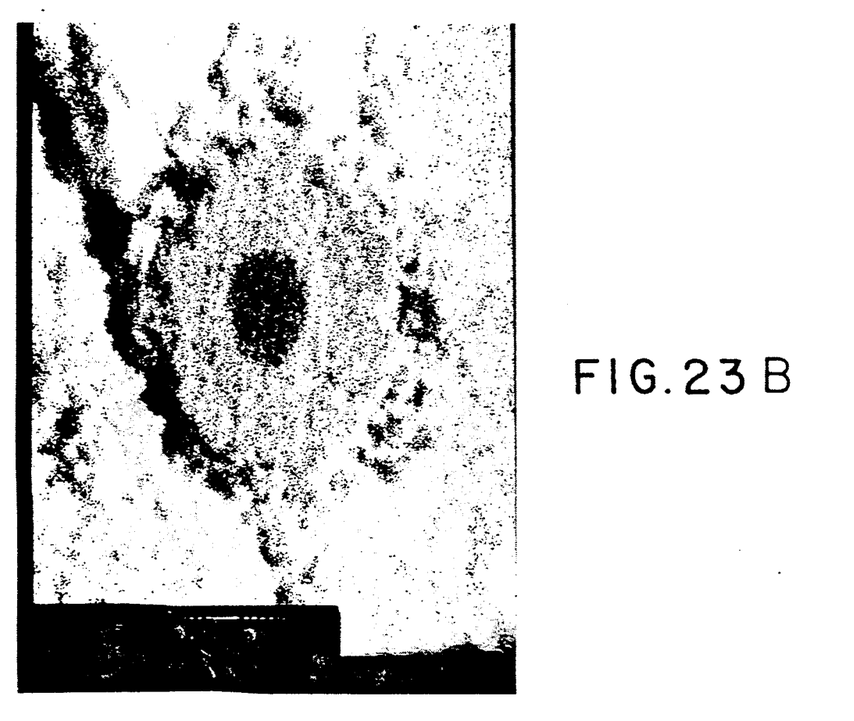

To check the electrodes 8 and 10 for the formation of Sn solid solution, sensors were tested for durability in the same reducing atmosphere as above and then disassembled. The electrodes 8, 10 were cut, and the distribution of Sn or Pt in the cut surface was determined. FIGS. 20 (A), (B) to FIGS. 23 (A), (B) show elementary analysis images (600×0.8) at 480X. Each photograph (A) shows the distribution of Pt, and each photograph (B) shows the distribution of Sn. FIG. 20 shows the images of BS16 free from MgCl$_2$(BaSnO$_3$ prepared under the same conditions as BS15 and identical with BS15 except the date of preparation). FIG. 21 shows the images of BS16 with addition of 0.2 mol of Mg ethylate. A comparison between FIGS. 20 and 21 reveals that even with the sample free from Si and B, formation of Sn solid solution in the electrode can be prevented more effectively by the presence of Mg. FIG. 22 shows the images of a sample prepared by intentionally adding Si(OC$_2$H$_5$)4 in an amount of 0.2 mol % calculated as Si to BS16, and FIG. 23 shows the images of a sample similarly prepared by the addition of 0.2 mol % of B. The B was added by impregnating BaSnO$_3$·3H$_2$O with ethanol solution of B$_2$O$_3$. In the Pt electrode portion shown, the bright dots corresponding to Sn indicate the diffused Sn.

With samples having Si and B added thereto, Sn diffuses markedly through Pt. The Sn solid solution formed in the Pt electrodes is closely related with Si or B. Other samples were also subjected to durability test in the reducing atmosphere and thereafter examined by the elementary analysis of cut electrode surfaces to chek Sn solid solution. In the experiments stated above no break occurred in the electrodes 8, 10.

TABLE 6

| Lot | Sn Solid Solution in Electrode<br>Sn solid solution formed |
|---|---|
| BS10 free from MgCl$_2$ | Sn solid solution over the entire electrode surface with Sn clusters of high density |
| BS10 with 0.2 mol % MgCl$_2$ | Thin Sn solid solution over the entire electrode surface |
| BS10 with 0.2 mol % CaCl$_2$ | Thin Sn solid solution over the entire electrode surface |

Supplement

Although BaSnO$_3$ typical of the compounds ASnO$_3$ has been described above with reference to embodiments or examples for illustrative purposes, BaSnO$_3$ may be replaced by SrSnO$_3$, CaSnO$_3$ or RaSnO$_3$ analogous thereto.

Mg or Ca is used in the foregoing embodiments as an additive which is low in electronegativity (basic) for modifying the surface of BaSnO$_3$ or the like to basicity. It is critical that the additive element be up to 1.3, preferably up to 1.2, in Pauling electronegativity. The additive is not limited to Mg or Ca but can be Sr, Ba, La, Sc or the like. The amount of the additive to be used is at least ⅓, preferably ½, of the combined content of Si and B in gram atom unit, because for example when 500 mol ppm of Mg is added to the lot BS13 containing a little over 1000 mol ppm of Si and 500 mol ppm B (see Table 1), the sensors obtained are diminished in variations in resistance value, have a high speed of response at low temperatures and possess high durability against various atmospheres.

In the examples, three methods are used for evaluation i.e., removal of Si or B, addition of Mg or Ca, and intentional addition of Si and B to the Si- and B-free material. Further investigations have been made of the variations produced by these methods in the acid base strength of the BaSnO$_3$ surface. The results achieved are comparable. Apparently, similar results can be achieved by removing Si or B, adding Mg or Ca, or controlling the acid-base strength of the BaSnO$_3$ surface.

The container lined with a synthetic resin and used in the invention is usable also for the liquid-phase preparation of other perovskite compounds such as SrTiO$_3$.

What is claimed is:

1. An exhaust gas sensor including a gas sensitive member comprising a compound ASnO$_3$ wherein A is at least one element selected from the group consisting of Ca, Sr, Ba and Ra, a heat-resistant insulating support member having the gas sensitive member supported thereon, and at least one pair of electrodes connected to the sensitive member, the exhaust gas sensor being characterized in that the compound ASnO$_3$ is free of segregation of the A element and Sn element and greater than 6.8 in acid-base strength as measured with Hammett's indicator in benzene.

2. An exhaust gas sensor including a gas sensitive member comprising a compound ASnO$_3$ wherein A is at least one element selected from the group consisting of Ca, Sr, Ba and Ra, a heat-resistant insulating support member having the gas sensitive member supported thereon, and at least one pair of electrodes connected to the sensitive member, the exhaust gas sensor being characterized in that the compound ASnO$_3$ is free of segregation of the A element and Sn element wherein the amount of Si and the amount of B present in said compound ASnO$_3$ as impurities is up to 200 mol ppm and up to 100 mol ppm respectively per mol of the ASnO$_3$.

3. An exhaust gas sensor including a gas sensitive member comprising a compound ASnO$_3$ wherein A is at least one element selected from the group consisting of Ca, Sr, Ba and Ra, a heat-resistant insulating support member having the gas sensitive member supported thereon, and at least one pair of electrodes connected to the sensitive member, wherein the amount of Si and the amount of B present in said compound ASnO$_3$ as impurities is up to 200 mol ppm and up to 100 mol ppm respectively per mol of the ASnO$_3$ the exhaust gas sensor being characterized in that the compound ASnO$_3$ is free of segregation of the A element and Sn element and having added hereto an element up to 1.3 in Pauling electronegativity in an amount of at least ⅓ of the combined amount of Si and B elements in the compound ASnO$_3$ in gram atom unit.

4. An exhaust gas sensor as defined in claim 3 wherein the combined Si and B content of the compound ASnO$_3$ is up to 300 mol ppm per mol of the compound ASnO$_3$, and the compound ASnO$_3$ has added thereto the element up to 1.3 in the electronegativity in an amount of 500 to 5000 mol ppm per mol of the compound ASnO$_3$.

* * * * *

UNITED STATES PATENT AND TRADEMARK OFFICE
CERTIFICATE OF CORRECTION

PATENT NO. : 5,070,318

DATED : December 3, 1991

INVENTOR(S) : Mariko Hanada, et al

It is certified that error appears in the above-identified patent and that said Letters Patent is hereby corrected as shown below:

On the Title page, Item [73] Assignee should read--Figaro Engineering, Inc, Osaka; and Mazda Motor Corporation, Hiroshima-Ken, both of Japan--.

Col. 14, line 57, change "hereto" to read --thereto--.

Signed and Sealed this

Sixth Day of April, 1993

*Attest:*

STEPHEN G. KUNIN

*Attesting Officer*    *Acting Commissioner of Patents and Trademarks*